US011547304B2

(12) United States Patent
Kim

(10) Patent No.: US 11,547,304 B2
(45) Date of Patent: Jan. 10, 2023

(54) COMPOSITE DEVICE FOR MEDICAL IMAGE CAPTURING

(71) Applicant: GOODDOCTORS CO., LTD., Incheon (KR)

(72) Inventor: Young Woon Kim, Bucheon-si (KR)

(73) Assignee: GOODDOCTORS CO., LTD., Incheon (KR)

( * ) Notice: Subject to any disclaimer, the term of this patent is extended or adjusted under 35 U.S.C. 154(b) by 464 days.

(21) Appl. No.: 16/625,829

(22) PCT Filed: May 31, 2018

(86) PCT No.: PCT/KR2018/006225
§ 371 (c)(1),
(2) Date: Dec. 23, 2019

(87) PCT Pub. No.: WO2019/022361
PCT Pub. Date: Jan. 31, 2019

(65) Prior Publication Data
US 2020/0146556 A1    May 14, 2020

(30) Foreign Application Priority Data

Jul. 28, 2017 (KR) .......................... 10-2017-0096008

(51) Int. Cl.
*A61B 1/00* (2006.01)
*A61B 5/00* (2006.01)
(Continued)

(52) U.S. Cl.
CPC ........ *A61B 5/0088* (2013.01); *A61B 1/00188* (2013.01); *A61B 1/042* (2013.01);
(Continued)

(58) Field of Classification Search
CPC ....... A61B 1/00; A61B 5/0088; A61B 1/0646; A61B 1/04; A61B 1/06; A61B 1/042;
(Continued)

(56) References Cited

U.S. PATENT DOCUMENTS 6,957,907 B2 * 10/2005 Fischer ................ A61B 5/0088
433/29
7,570,984 B2    8/2009 Katsuda et al.
(Continued)

FOREIGN PATENT DOCUMENTS

JP         3370912       11/2002
JP         2011-172609    9/2011
(Continued)

*Primary Examiner* — Timothy J Neal
*Assistant Examiner* — Sung Ham
(74) *Attorney, Agent, or Firm* — Lex IP Meister, PLLC

(57) ABSTRACT

A composite device for medical image capturing according to the present invention includes: a head part including a camera unit provided with an image sensor to capture a tooth image, a printed circuit board for operation control of the camera unit and signal transmission therefrom, a light source panel having multiple light sources mounted therein, the light sources emitting light towards a target tooth of which an image is to be captured by the camera unit, an upper housing having the camera unit, the printed circuit board, and the light source panel which are embedded therein, and a lower housing; and a main body part provided with an operation panel for signal input, and supplying electric power to the head part and transmitting a tooth image signal received from the head part to outside.

3 Claims, 11 Drawing Sheets

(51) Int. Cl.
*A61B 1/04* (2006.01)
*A61B 1/05* (2006.01)
*A61B 1/06* (2006.01)

(52) U.S. Cl.
CPC .............. *A61B 1/05* (2013.01); *A61B 1/0638* (2013.01); *A61B 1/0646* (2013.01)

(58) Field of Classification Search
CPC ..... A61B 5/4547; A61B 1/00188; A61B 1/05; A61B 1/24; A61B 5/0071; A61B 1/0638; H02J 7/00
See application file for complete search history.

(56) References Cited

U.S. PATENT DOCUMENTS

| | | | | |
|---|---|---|---|---|
| 2005/0003323 | A1* | 1/2005 | Katsuda | A61B 1/0676 433/29 |
| 2006/0152586 | A1* | 7/2006 | Komiya | A61C 13/082 348/E5.029 |
| 2011/0102566 | A1* | 5/2011 | Zakian | A61B 5/0086 348/66 |
| 2011/0149058 | A1* | 6/2011 | Liang | A61B 1/043 348/66 |
| 2011/0221878 | A1* | 9/2011 | Kitaoka | A61B 1/0676 348/66 |
| 2013/0034826 | A1* | 2/2013 | Walsh | A61B 1/0607 433/29 |
| 2014/0272764 | A1* | 9/2014 | Miller | A61B 1/0684 433/29 |
| 2014/0313299 | A1* | 10/2014 | Gebhardt | A61B 1/24 348/66 |
| 2015/0250572 | A1* | 9/2015 | Gramann | A61B 1/0655 433/29 |
| 2018/0080828 | A1* | 3/2018 | Fink | A61B 5/1034 |

FOREIGN PATENT DOCUMENTS

| | | |
|---|---|---|
| KR | 10-1618684 | 4/2016 |
| KR | 20160041632 A * | 4/2016 |
| KR | 10-1717284 | 3/2017 |

* cited by examiner

[Fig. 1]
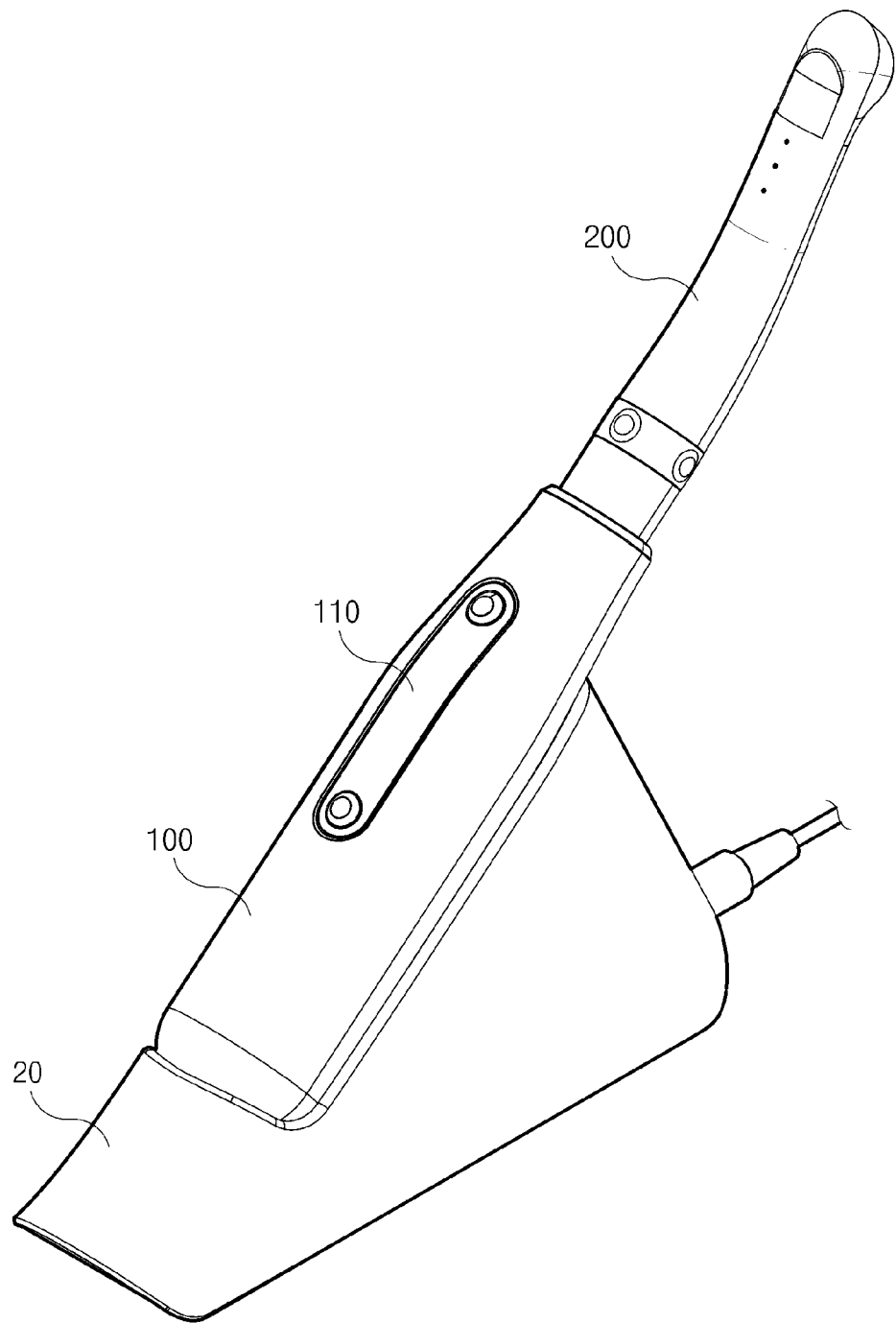

[Fig. 2]
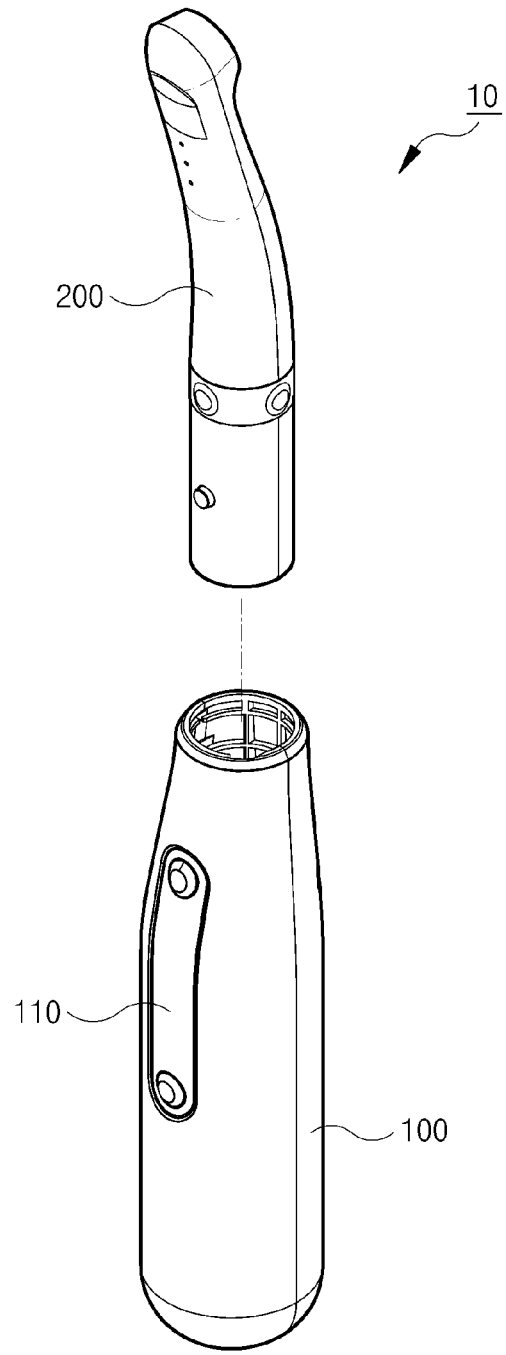

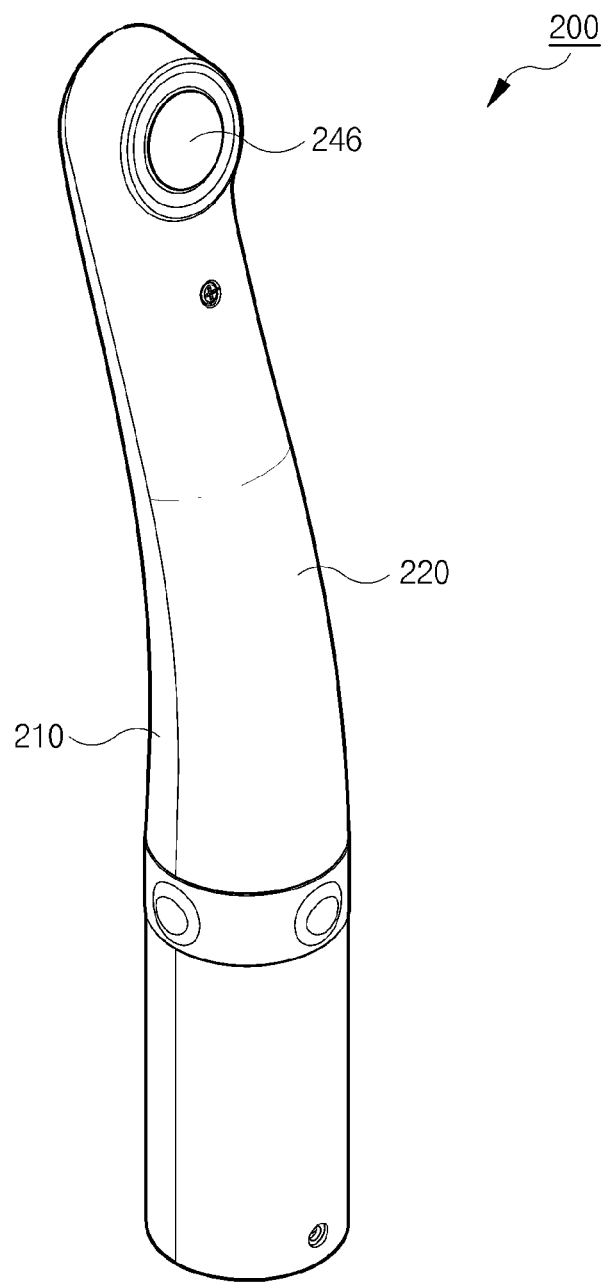
[Fig. 3]

[Fig. 4]
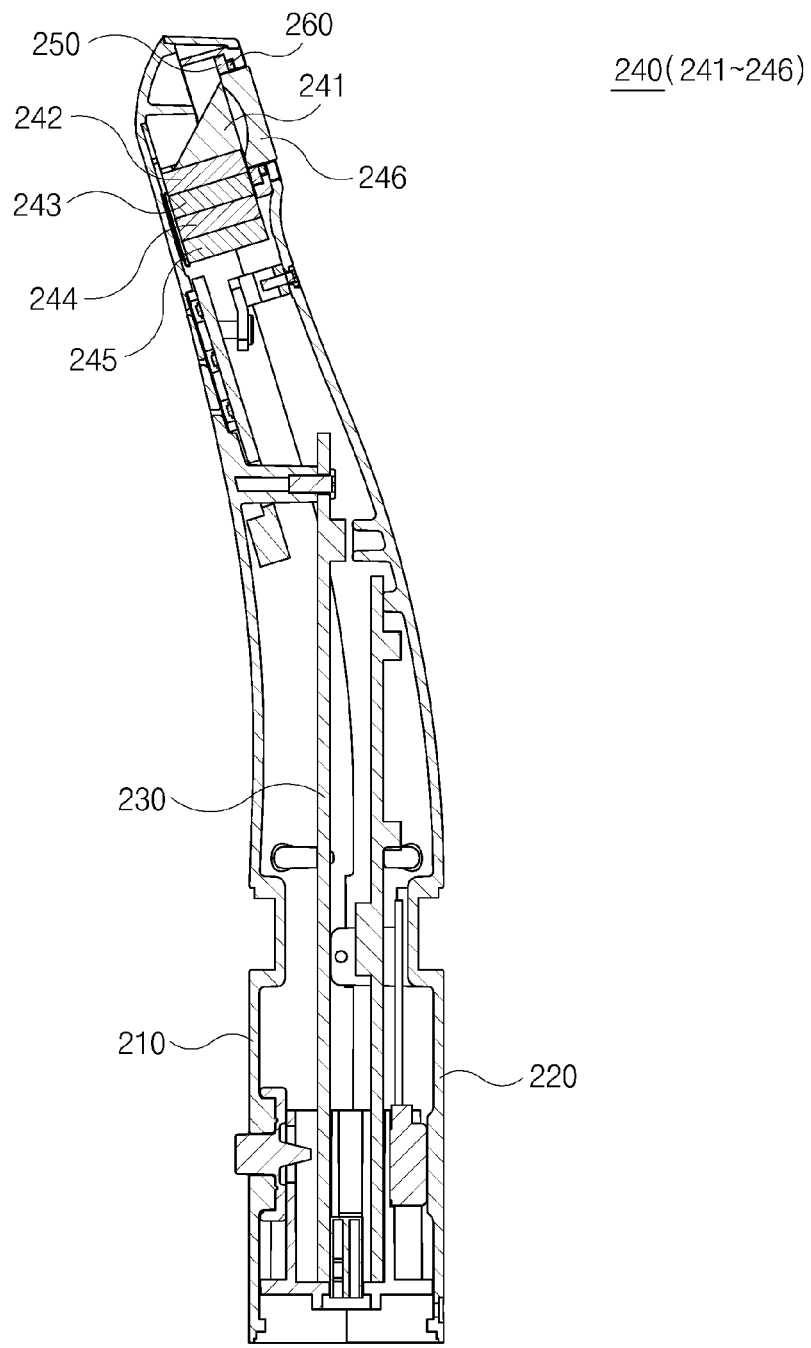

[Fig. 5]
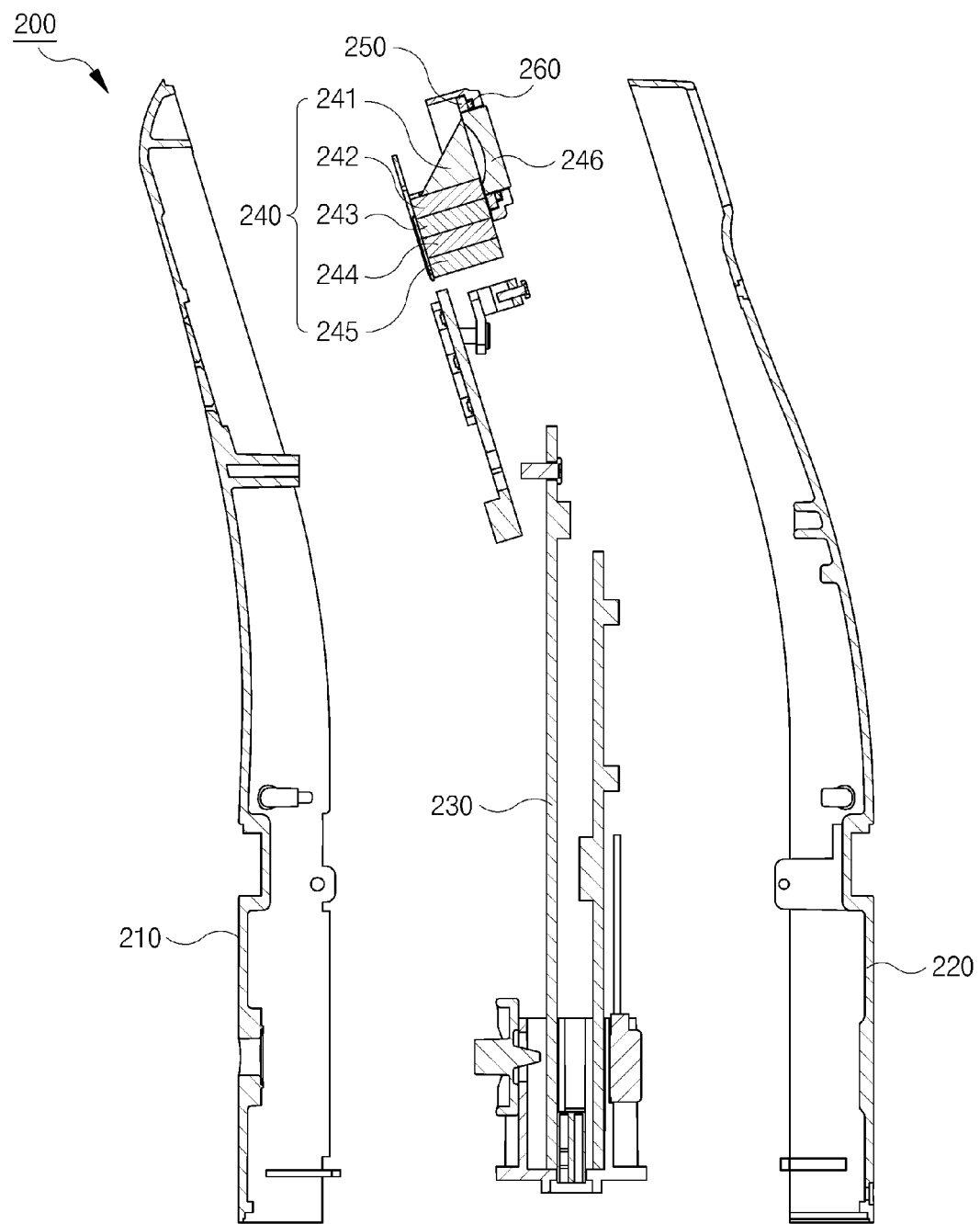

[Fig. 6]
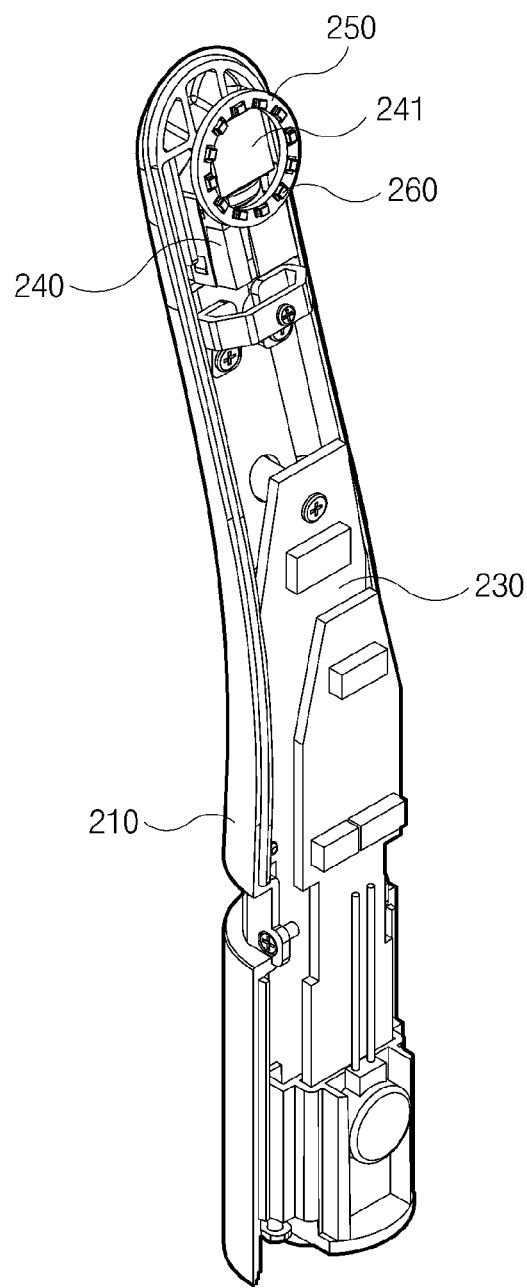

[Fig. 7]
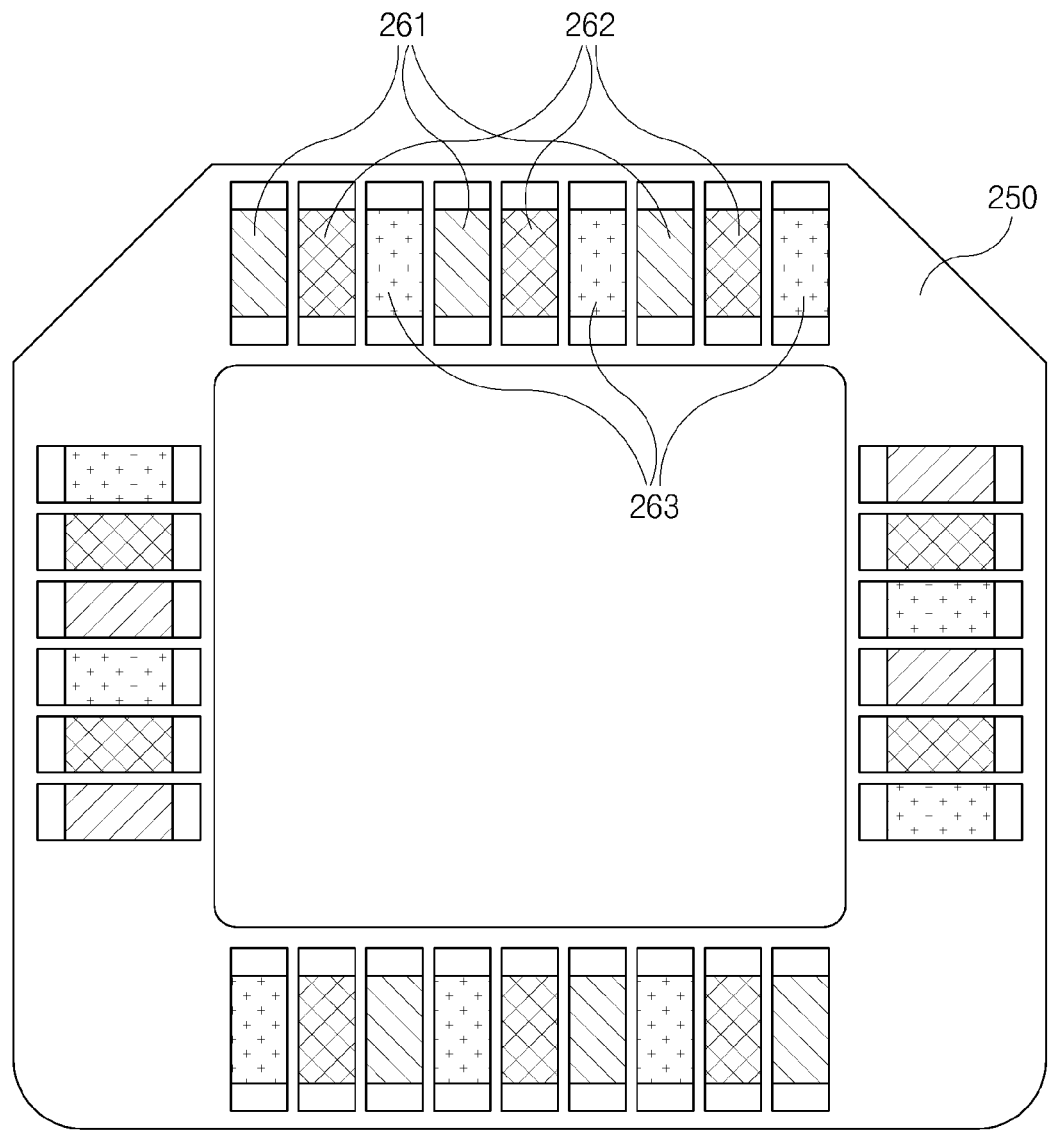

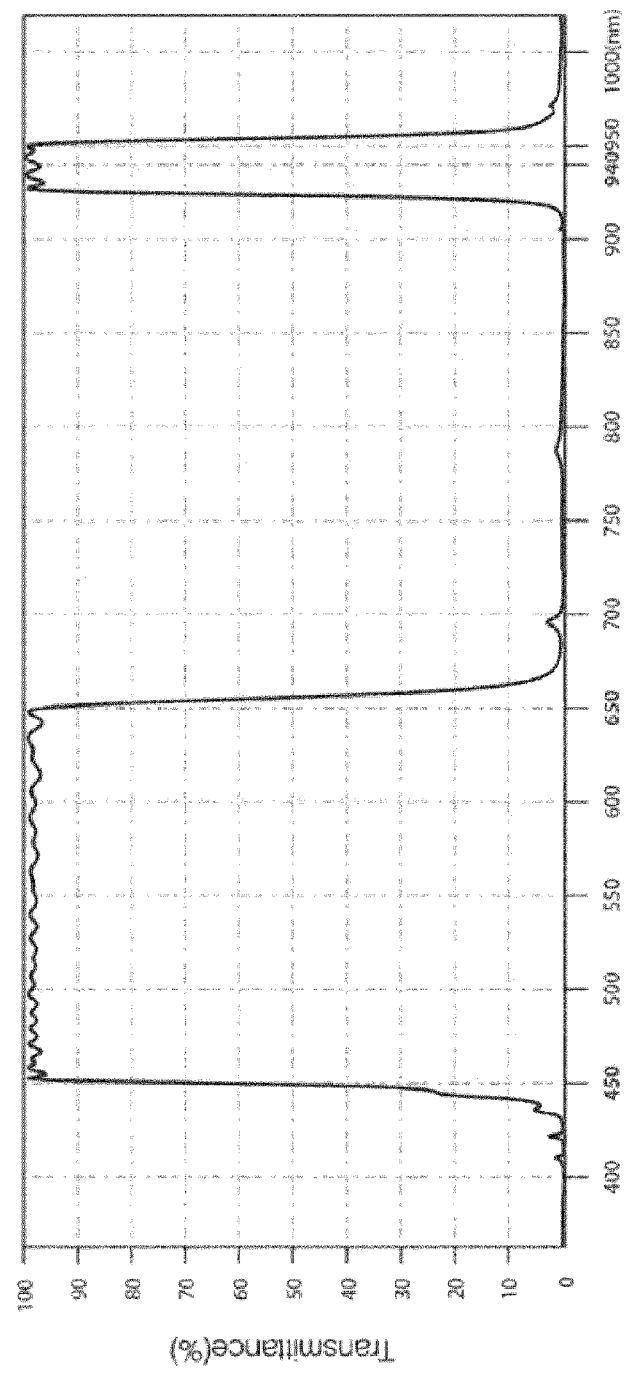
[Fig. 8]

[Fig. 9]
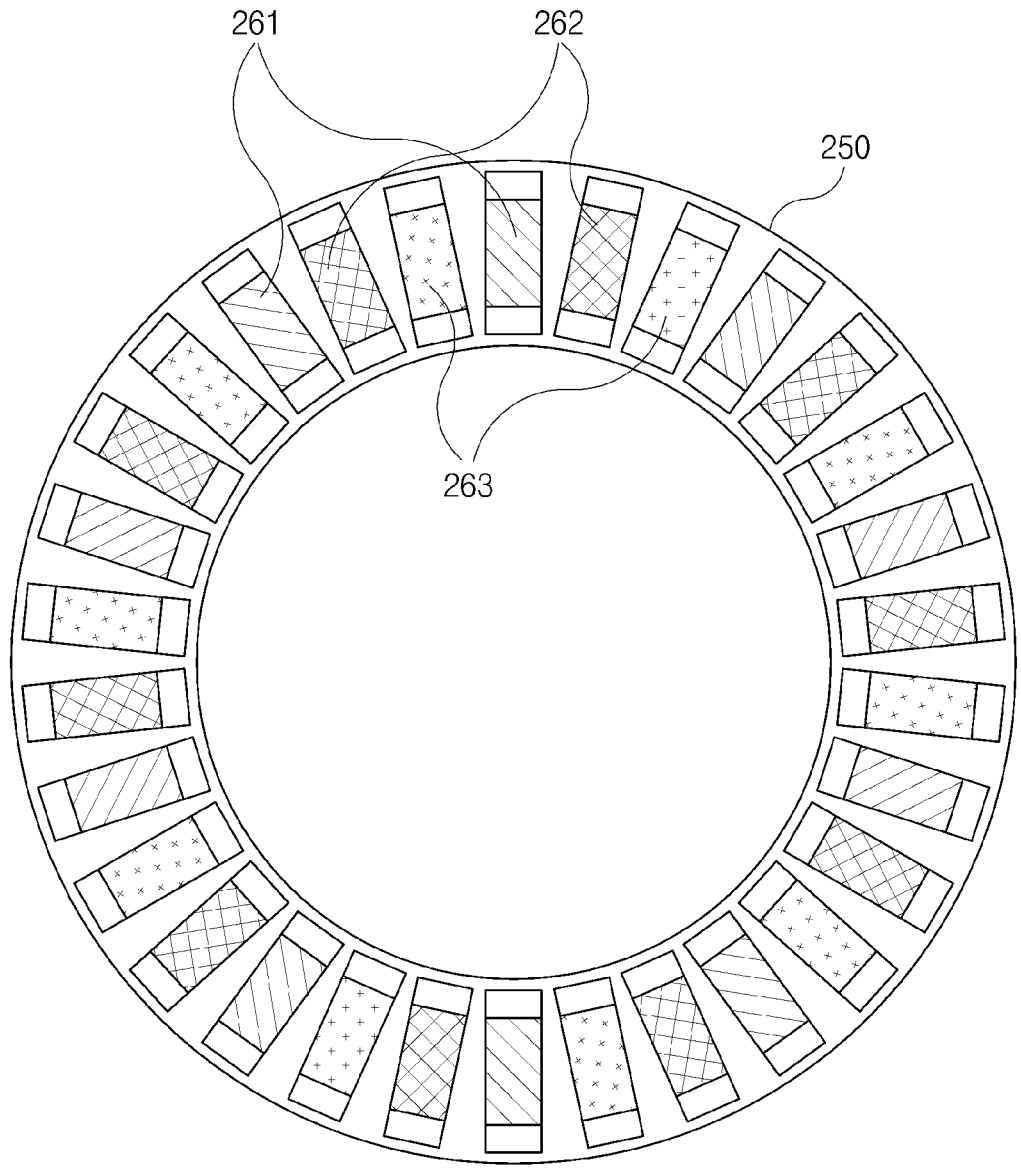

[Fig. 10]
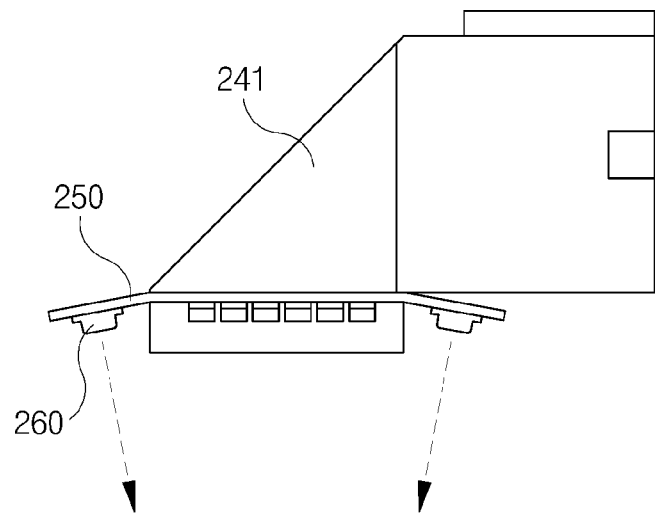
[Fig. 11]
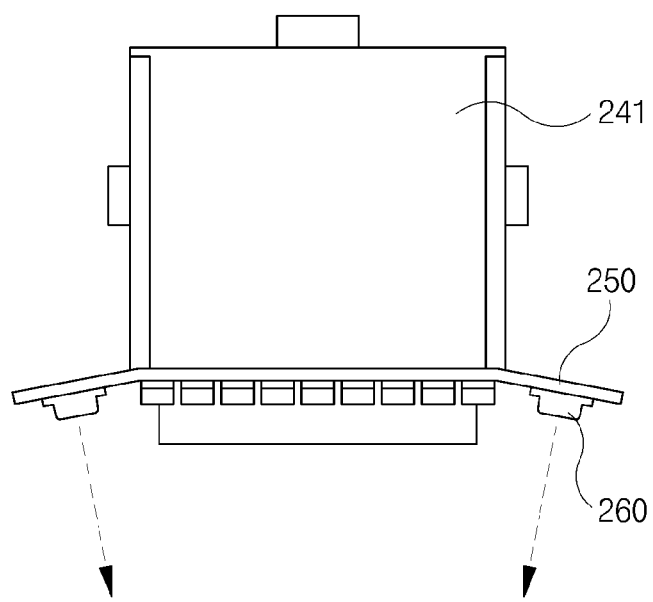

[Fig. 12]
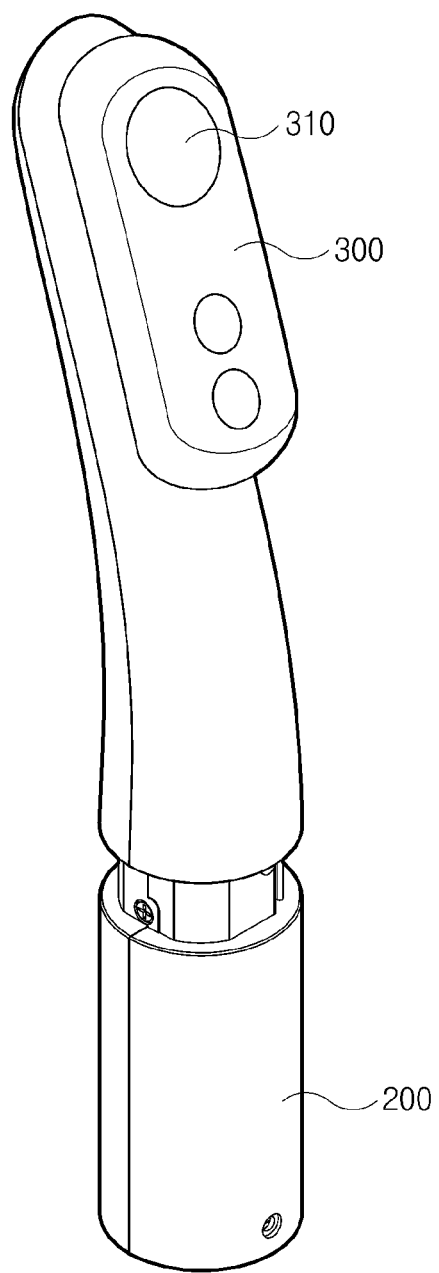

COMPOSITE DEVICE FOR MEDICAL IMAGE CAPTURING

TECHNICAL FIELD

The present invention relates generally to a device for medical image capturing of a tooth or an oral cavity. More particularly, the present invention relates to a composite device for medical image capturing, which is configured to be capable of capturing a tooth image in various ways without requiring replacement of parts.

BACKGROUND ART

As well known in the art, to establish an accurate diagnosis for oral lesions of a patient, an image of the overall appearance of a patient including the patient's face (portrait) and an image of tooth contours including an image of all the teeth, an image of each tooth, a close-up enlarged image of a specific portion of one tooth, and the like are required.

Meanwhile, for early caries detection, there has been developed a technique of detecting caries at an early stage of development using fluorescence generated by tooth tissue under light having a specific wavelength (about 405 nm). This is called "quantitative light-induced fluorescence". This is a method of quantitatively measuring the degree of caries using fluorescence spectra, in which a healthy tooth appears bright green in a fluorescence image, while a lesion such as dental caries appears dark on a bright green background, thus diagnosing dental caries.

Furthermore, there has been developed another image capturing method for early caries detection using transillumination, in which a tooth image is captured in a state in which near-infrared light having a wavelength range of 800 nm to 1300 nm is emitted to a tooth, thus illuminating the inside of the tooth. This method is advantageous to detect caries located at interproximal contact sites between adjacent teeth and detect cracks in teeth.

As described above, in order to accurately diagnose the state of a tooth, an image of tooth contours, a tooth image captured using quantitative light-induced fluorescence, and a tooth image captured using transillumination are separately required. To obtain these various types of tooth images, in the related art, a camera device for capturing the image of tooth contours, an image capturing camera device using quantitative light-induced fluorescence, and an image capturing camera device using transillumination are separately required, causing user's inconvenience and an increase in purchasing cost.

In an effort to solve such a problem, a multi-camera for medical treatment (Korean Patent No. 10-1618684), which is capable of selectively combining multiple head parts emitting wavelengths of different bands for image capturing, was proposed by the present applicant.

However, such a multi-camera for medical treatment has a disadvantage in that it is required to replace the head parts according to a change in image capturing method, causing inconvenience to capturing of a tooth image. Additionally, each head part is detachably coupled to a main body of the camera, causing frequent loss or breakage of the head part.

DISCLOSURE

Technical Problem

Accordingly, the present invention has been made keeping in mind the above problems occurring in the related art, and an objective of the present invention is to provide a composite device for medical image capturing, the device being capable of capturing a tooth image in various ways without requiring replacement of a head part, thus making it possible to shorten examination time for early caries detection and to prevent loss and breakage of the head part, while achieving a reduction in manufacturing costs.

Technical Solution

In order to accomplish the above objective, according to an aspect of the present invention, there is provided a composite device for medical image capturing, the device being used for intraoral tooth image capturing and early caries detection and including: a head part including a camera unit provided with an image sensor to capture a tooth image, a printed circuit board for operation control of the camera unit and signal transmission therefrom, a light source panel having multiple light sources mounted therein, the light sources emitting light towards a target tooth of which an image is to be captured by the camera unit, an upper housing having the camera unit, the printed circuit board, and the light source panel which are embedded therein, and a lower housing; and a main body part provided with an operation panel for signal input, and supplying electric power to the head part and transmitting a tooth image signal received from the head part to outside, wherein the multiple light sources include a first light source for emitting white light, a second light source for emitting light having a wavelength range of 380 nm to 420 nm, and a third light source for emitting light having a wavelength range of 800 nm to 1300 nm, and the camera unit is provided with a dual-bandpass filter manufactured to be capable of transmitting light having a wavelength range of 450 nm to 650 and light having a wavelength range of 800 nm to 1300 nm and mounted at a front side of the image sensor.

The prism lens may be configured such that a tooth image incident surface faces downward and a tooth image output surface faces rearward, and the light source panel may be formed to surround the incident surface of the prism lens and mounted such that the multiple light sources emit light downward.

The first light source, the second light source, and the third light source may be alternately arranged to surround the incident surface of the prism lens.

The light source panel may have an edge portion bent or curved downward, and the multiple light sources may be mounted on the bent or curved portion of a bottom surface of the light source panel and emit light in a direction inclined toward a center of an incident area of the prism lens.

The camera unit may further include: an autofocus lens seated on an output surface of the prism lens; and an image lens mounted between the autofocus lens and the dual-bandpass filter.

The device may further include: a long-distance image capturing unit coupled to the head part in an attachable and a detachable manner and provided with a reinforcing lens for long-distance image capturing at a portion covering an incident surface of the prism lens.

The main body part may be provided with a rechargeable battery rechargeable through a charging cradle.

According to another aspect of the present invention, there is provided a composite device for medical image capturing, the device being used for intraoral tooth image capturing and early caries detection.

The composite device for medical image capturing includes a head part including a camera unit provided with an image sensor to capture a tooth image, a printed circuit board for operation control of the camera unit and signal transmission therefrom, a light source panel having at least one light source mounted therein, the light sources emitting light towards a target tooth of which an image is to be captured by the camera unit, an upper housing having the camera unit, the printed circuit board, and the light source panel which are embedded therein, and a lower housing; and a main body part provided with an operation panel for signal input, and supplying electric power to the head part and transmitting a tooth image signal received from the head part to outside, wherein the at least one light source is a light source emitting light having a wavelength range of 380 fill to 1300 nm, and the camera unit is provided with a dual-bandpass filter manufactured to be capable of transmitting light having a wavelength range of 450 nm to 650 and light having a wavelength range of 800 nm to 1300 nm and mounted at a front side of the image sensor, the camera unit being further provided with: a first wavelength filter allowing only light having a wavelength range of 380 nm to 420 nm to be emitted from the light source; and a second wavelength filter allowing only light having a wavelength range of 800 nm to 1300 nm to be emitted from the light source.

Advantageous Effects

As described above, the composite device for medical image capturing according to the present invention can be used to capture a tooth image in various ways without requiring replacement of a head part, thus making it possible to shorten examination time for early caries detection and to prevent loss and breakage of the head part, while enabling image capturing in various ways with a single head and thus achieving a reduction in manufacturing costs.

DESCRIPTION OF DRAWINGS

FIG. 1 is a perspective view showing composite device for medical image capturing according to the present invention.

FIG. 2 is an exploded perspective view showing composite device for medical image capturing according to the present invention.

FIG. 3 is a perspective view showing a head part included in the composite device for medical image capturing according to the present invention.

FIG. 4 is a sectional view showing the head part included in the composite device for medical image capturing according to the present invention.

FIG. 5 is an exploded sectional view showing the head part included in the composite device for medical image capturing according to the present invention.

FIG. 6 is a perspective view showing an internal structure of the head part included in the composite device for medical image capturing according to the present invention.

FIG. 7 is a bottom view showing a first embodiment of a light source panel included in the composite device for medical image capturing according to the present invention.

FIG. 8 is a graph showing transmittance of a dual-bandpass filter included in the composite device for medical image capturing according to the present invention.

FIG. 9 is a bottom view showing a second embodiment of the light source panel included in the composite device for medical image capturing according to the present invention.

FIGS. 10 and 11 are a side view and a front view showing a mounting structure of a third embodiment of the light source panel included in the composite device for medical image capturing according to the present invention.

FIG. 12 is a perspective view showing a mounting structure of a long-distance image capturing unit included in the composite device for medical image capturing according to the present invention.

MODE FOR INVENTION

Hereinafter, exemplary embodiments of a composite device for medical image capturing according to the present invention will be described in detail with reference to the accompanying drawings.

FIG. 1 is a perspective view showing composite device for medical image capturing according to the present invention, FIG. 2 is an exploded perspective view showing composite device for medical image capturing according to the present invention, FIG. 3 is a perspective view showing a head part included in the composite device for medical image capturing according to the present invention, FIG. 4 is a sectional view showing the head part included in the composite device for medical image capturing according to the present invention, and FIG. 5 is an exploded sectional view showing the head part included in the composite device for medical image capturing according to the present invention.

The composite device 10 for medical image capturing according to the present invention is a type of a medical capturing device for intraoral tooth image capturing early caries detection and is mainly divided into a main body part 100 and a head part 200. The main body part 100 is provided with an operation panel 110 for signal input and serves to supply electric power to the head part 200 and transmit an operation signal to the head part 200 as well as transmitting a tooth image signal received from the head part 200 to the outside. The main body part 100 for performing such a function is equipped with a controller for processing a signal input by a user, a substrate for signal transmission, and the like. The internal structure of the main body part 100 as described above is substantially the same as that of a conventional medical camera device, and a detailed description of the internal structure of the main body part 100 is omitted.

Herein, the most distinctive feature of the composite device 10 for medical image capturing according to the present invention is that it is possible to capture a tooth image in various ways without requiring replacement of the head part 200 being mounted. In other words, the head part 200 includes: a camera unit 240 provided with an image sensor 245 to capture a tooth image; a printed circuit board 230 for operation control of the camera unit 240 and signal transmission therefrom; a light source panel 250 having multiple light sources 260 mounted therein, the light sources emitting light towards a target tooth of which an image is to be captured by the camera unit 240; an upper housing 210 having the camera unit 240, the printed circuit board 230, and the light source panel 250 which are embedded therein; and a lower housing 220, wherein the multiple light sources 260 are configured to emit light of different wavelength ranges, and which is a first feature of the present invention. For example, the multiple light sources 260 include a first light source 261 for emitting white light, a second light source 262 for emitting light having a wavelength range of 380 nm to 420 nm, and a third light source 263 for emitting light having a wavelength range of 800 nm to 1300 nm (see FIGS. 7 and 9).

The light source 260 may include a light emitting diode (LED), a laser light source, a halogen lamp, and other light sources capable of emitting light.

In order to acquire a tooth image using quantitative light-induced fluorescence (QLF), light having a wavelength range of 400 nm to 410 nm is required, and in order to acquire a tooth image using transillumination, light having a wavelength range of 800 nm to 1300 nm is required. The composite device 10 for medical image capturing according to the present invention can selectively emit white light, light having a wavelength range of 400 nm to 410 nm, and light having a wavelength range of 800 nm to 1300 nm without requiring replacement of the head part 200. This is advantageous to perform general image capturing, image capturing using QLF, and image capturing using transillumination.

Herein, the camera unit 240 is provided with a dual-bandpass filter 244 transmits light having a wavelength range of 450 nm to 650 nm and light having a wavelength range of 800 nm to 1300 nm, such that a general intraoral image, a tooth image captured using QLF, and a tooth image captured using transillumination are transmitted. The dual-bandpass filter 244 will be described later in detail with reference to FIG. 8.

Meanwhile, the prism lens 241 constituting the camera unit 240 is manufactured to have a right triangular cross section such that a tooth image incident surface faces downward and a tooth image output surface faces rearward. There is further provided a condenser lens 246 for condensing light at the incident surface-side of the prism lens 241 (the lower surface in FIG. 4). The condenser lens 246 is mounted so as to protrude through the lower housing 220. Furthermore, without provision of the condenser lens 246, only the prism lens 241 can be mounted such that the incident surface of the prism lens 241 protrudes through the lower housing 220.

Herein, the light source panel 250 is formed in a closed curve or closed polygonal shape surrounding the incident surface of the prism lens 241, such that light is uniformly emitted over a target tooth of which an image is to be captured (more precisely, a tooth of which an image is incident upon the prism lens 241). The multiple light sources 260 emitting light are mounted on the bottom surface of the light source panel 250, thus uniformly emitting light in each orientation of the target tooth of which an image is to be captured.

Furthermore, the camera unit 240 further includes an autofocus lens 242 seated on the output surface of the prism lens 241 and an image lens 243 mounted between the autofocus lens 242 and the dual-bandpass filter 244.

The autofocus lens 242 is a component which automatically adjusts the focus of image information incident through the prism lens 241 and may be a liquid lens or a lens using a voice coil motor (VCM). Through provision of the autofocus lens 242 being mounted on the output surface of the prism lens 241 as described above makes it possible to obtain a focused tooth image only by operation of positioning a tip end-side of the head part 200 (more precisely, a portion where the incident surface of the prism lens 241 is located) in the oral cavity of a patient without performing separate focusing operation. Meanwhile, the image lens 243 is applied to a general image capturing device in a substantially same manner, and a detailed description of the image lens 243 will be omitted.

The dual-bandpass filter 244 is configured to be positioned at the front side of the image sensor 245, and the image sensor 245 may be a variety of image sensors, including a charge-coupled device (CCD), complementary metal-oxide-semiconductor (CMOS) device, or the like.

The main body part 100 may be configured to receive and supply electric power to be delivered to the head part 200 in a wired manner and may be provided with a rechargeable battery (not shown) rechargeable through a charging cradle 20 such that the electric power is supplied in a wireless manner. Herein, the charging cradle 20 has a mounting groove formed therein such that a portion of an end of the main body part 100 is inserted thereinto, and a charging terminal for supplying a charging terminal for supplying a charging current is provided in the mounting groove. At present, the charging cradle 20 as described above is commercially available for various purposes, and a detailed description of a process of charging the device for medical image capturing according to the present invention through the charging cradle 20 will be omitted.

FIG. 6 is a perspective view showing an internal structure of the head part 200 included in the composite device 10 for medical image capturing according to the present invention, FIG. 7 is a bottom view showing a first embodiment of the light source panel 250 included in the composite device 10 for medical image capturing according to the present invention, and FIG. 8 is a graph showing transmittance of the dual-bandpass filter 244 included in the composite device 10 for medical image capturing according to the present invention.

The first feature of the composite device 10 for medical image capturing according to the present invention is that the device is not composed of one type of light source 260 for applying light to a target tooth of which an image is to be captured, but various types of light sources emitting light of different wavelength ranges.

In other words, the light source panel 250 is configured such that the first light source 261 emitting white light, the second light source 262 emitting light having a wavelength range of 380 nm to 420 nm, and the third light source 263 emitting light having a wavelength range of 800 nm to 1300 nm are positioned together. Herein, the first light source 261, the second light source 262, and the third light source 263 are alternately arranged to surround the incident surface of the prism lens 241, such that even when one light source of the first light source 261, the second light source 262, and the third light source 263 is turned on, light is uniformly applied to each part of a tooth.

Meanwhile, when it is required to capture a general intraoral image or intraoral tooth image, the first light source 261 is operated to emit white light. To allow the white light to pass through the dual-bandpass filter 244 to be transmitted to the image sensor 245, the dual-bandpass filter 244 is manufactured to have a structure capable of transmitting light having a wavelength range of 450 nm to 650 nm.

Furthermore, when it is required to capture a tooth image with the composite device 10 for medical image capturing according to the present invention on the basis of QLF, the second light source 262 is operated to emit green light having a wavelength range of 380 nm to 420 nm to a tooth. This light is scattered and appears dark at an early caries lesion in a tooth, while the light is scattered and appears red at a lesion, such as plaques, calculus, cracks, and caries in a tooth, and the like. To allow the light scattered and appearing dark or red as described above to pass through the dual-bandpass filter 244 to be transmitted to the image sensor 245, the dual-bandpass filter 244 is manufactured to have a structure capable of transmitting light having a wavelength range of 450 nm to 650 nm.

Furthermore, when it is required to capture a tooth image with the composite device 10 for medical image capturing according to the present invention on the basis of transillumination, the third light source 263 is operated to emit light having a wavelength range of 800 nm to 1300 nm to a tooth, thus illuminating the inside of the tooth which appears transparent. The light having a wavelength range of 800 nm to 1300 nm as described above is transmitted to the image sensor 245 without a change in wavelength. Because of this, the dual-bandpass filter 244 is manufactured to be capable of transmitting light having a wavelength range of 800 nm to 1300 nm.

In other words, it is preferable that the dual-bandpass filter 244 is manufactured to be capable of transmitting both light having a wavelength range of 450 nm to 650 nm and light having a wavelength range of 800 nm to 1300 nm. Herein, although FIG. 8 shows only the transmittance of the dual-bandpass filter 244 capable of transmitting light having a wavelength range of 450 nm to 650 nm and light having a wavelength range of 930 nm to 950 nm, the transmission wavelength range of the dual-bandpass filter 244 can be variously changed according to various conditions, such as the type of light source 260, the characteristics of a target tooth of which an image is to be captured, and the like.

According to another embodiment of the present invention, instead of the dual-bandpass filter, a filter film having the same effect as that of the dual-bandpass filter is coated or attached on the surface of the image lens 243 so as to be positioned at the front side of the image sensor 245.

Meanwhile, the composite device 10 for medical image capturing according to the present invention may be configured to selectively operate only one light source of the first light source 261, the second light source 262, and the third light source 263, or a combination of two or more light sources of the first light source 261, the second light source 262, and the third light source 263 for multiple image capturing. For example, a tooth image is captured in a state in which the second light source 262 and the third light source 263 are operated, whereby it is possible to simultaneously perform tooth image capturing using QLF and tooth image capturing using transillumination.

Furthermore, the composite device 10 for medical image capturing according to the present invention may be set to automatically sequentially perform general tooth image capturing, tooth image capturing using QLF, and tooth image capturing using transillumination or simultaneously perform such three image capturing. In other words, the composite device 10 for medical image capturing according to the present invention may be set to perform image capturing in accordance with a capturing mode selected by a user.

FIG. 9 is a bottom view showing a second embodiment of the light source panel 250 included in the composite device 10 for medical image capturing according to the present invention, and FIGS. 10 and 11 are a side view and a front view showing a mounting structure of a third embodiment of the light source panel 250 included in the composite device 10 for medical image capturing according to the present invention.

In a case where the light source panel 250 surrounding the incident surface of the prism lens 241 is formed in a quadrangular frame shape as shown in FIG. 7, even if the multiple light sources 260 are arranged in a dense configuration, it is impossible for the light sources 260 to be provided at the corners of the light source panel. Because of this, light may not be sufficiently applied to a side of a target tooth of which an image is to be captured, the side of the target tooth corresponding to the corner of the light source panel 250. Thus, as shown in FIGS. 6 and 9, in the composite device 10 for medical image capturing according to the present invention, the light source panel 250 is manufactured in a ring shape so as to uniformly apply light to each part of a target tooth of which an image is to be captured.

Meanwhile, when the light source panel 250 is formed to define a single flat surface, the light sources 260 mounted on the bottom surface of the light source panel 250 emit light in a downward vertical direction, and thus an area under the incident surface of the prism lens 241 becomes relatively low in illuminance. Herein, when it is required to capture a tooth image with the composite device 10 for medical image capturing, the incident surface of the prism lens 241 is positioned over a target tooth. In a case where the light sources 260 are set to emit light vertically downward as described above, the periphery of the target tooth becomes brighter while the target tooth becomes relatively dark. This is due to the fact that the light sources 260 are arranged to surround the prism lens 241.

Thus, as shown in FIGS. 10 and 11, the composite device 10 for medical image capturing according to the present invention is configured such that the light source panel 250 has an edge portion bent or curved downward, such that the multiple light sources 260 brightly illuminate a target tooth of which an image is to be captured.

When the edge portion of the light source panel 250 is bent or curved downward as described above, the multiple light sources 260 are mounted on the bent or curved portion of the bottom surface of the light source panel 250. Accordingly, as shown in FIGS. 10 and 11, each light source 260 emits light in a direction inclined toward the center of the incident area of the prism lens 241.

When the light emitting direction of each light source 260 is set so as to be inclined toward the center of the incident area of the prism lens as described above, light can be concentrated on a target tooth of which an image is to be captured, thus making it possible to more accurately capture a tooth image. Herein, the angle of bending or curvature of the light source panel 250 can be properly determined in consideration of the incident area of the prism lens.

FIG. 12 is a perspective view showing a mounting structure of a long-distance image capturing unit 300 included in the composite device 10 for medical image capturing according to the present invention.

The composite device 10 for medical image capturing according to the present invention is manufactured to be suitable for close-up image capturing and thus is unsuitable for capturing an image of all the teeth of a patient at one time.

Accordingly, the composite device 10 for medical image capturing according to the present invention further includes the long-distance image capturing unit 300 coupled to the head part 200 so as to enable long-distance image capturing. The long-distance image capturing unit 300 is coupled to the tip end-side of the head part 200 in an attachable and a detachable manner and is provided with a reinforcing lens 310 for long-distance image capturing at a portion covering the incident surface of the prism lens 241. Thus, as shown in FIG. 12, in a state in which the long-distance image capturing unit 300 is coupled to the head part 200, it is possible to capture an image of all the teeth or the oral cavity of a patient, that is, to perform long-distance image capturing.

In the embodiments of the present invention, the multiple light sources are provided on the light source panel 250. However, in a further embodiment of the present invention, the light source panel 250 is provided with at least one light source (e.g., a halogen lamp or the like) which emits light having a wavelength range of 380 nm to 1300 nm. In this case, to obtain a tooth image using QLF, there may be additionally required provision of a first wavelength filter allowing only light having a wavelength range of 380 nm to 420 nm to pass therethrough to be emitted from the light source, while to obtain a tooth image using transillumination, there may be additionally required provision of a second wavelength filter allowing only light having a wavelength range of 800 nm to 1300 nm to pass therethrough to be emitted from the light source. The first wavelength filter and the second wavelength filter may refer to filters that allow only light having a specific wavelength range to pass therethrough. The configurations other than the above-described light source are as described with reference to FIGS. 1 to 12.

In a case where the light source panel 250 is provided with a light source emitting light having a wavelength range of 380 nm to 1300 nm, the first wavelength filter and the second wavelength filter are properly controlled to adjust the wavelength range of light being emitted, thus making it possible to obtain a general intraoral image, a tooth image captured using QLF, and a tooth image captured using transillumination.

In still another embodiment, in a case where light being emitted from a light source is changeable in wavelength, that is, in a case where a light source capable of changing the wavelength of light being emitted is provided, a single light source is used to emit light having a desired wavelength as required, thus making it possible to obtain a general intraoral image, a tooth image captured using QLF, and a tooth image captured using transillumination.

While the exemplary embodiments of the invention have been described above, it will be understood by those skilled in the art that the invention can be modified in various forms without departing from the scope and spirit of the invention. Therefore, the scope of the invention should be determined on the basis of the descriptions in the appended claims, rather than any specific embodiment.

The invention claimed is:

1. A composite device for medical image capturing, the device being used for intraoral tooth image capturing and early caries detection and comprising:
a head part including a camera unit provided with an image sensor to capture a tooth image, a printed circuit board for operation control of the camera unit and signal transmission therefrom, a light source panel having multiple light sources mounted therein, the light sources emitting light towards a target tooth of which an image is to be captured by the camera unit, an upper housing having the camera unit, the printed circuit board, and the light source panel which are embedded therein, and a lower housing; and
a main body part provided with an operation panel for signal input, and supplying electric power to the head part and transmitting a tooth image signal received from the head part to outside,
wherein the multiple light sources include a first light source for emitting white light, a second light source for emitting light having a wavelength range of 380 nm to 420 nm, and a third light source for emitting light having a wavelength range of 800 nm to 1300 nm, and
the camera unit is provided with a dual-bandpass filter manufactured to be capable of transmitting light having a wavelength range of 450 nm to 650 and light having a wavelength range of 800 nm to 1300 nm and mounted at a front side of the image sensor, a prism lens having a tooth image incident surface facing downward and a tooth image output surface facing rearward, an autofocus lens seated on the tooth image output surface of the prism lens, and an image lens mounted between the autofocus lens and the dual-bandpass filter
wherein the light source panel is formed to surround the tooth image incident surface of the prism lens and mounted such that the multiple light sources emit light downward,
wherein the light source panel has an edge portion bent or curved downward, and
the multiple light sources are mounted on the bent or curved portion of a bottom surface of the light source panel and emit light in a direction inclined toward a center of an incident area of the prism lens,
wherein the composite device simultaneously turns on at least two of the first light source, the second light source, and the third light source and simultaneously captures at least two of an image of tooth contours, a tooth image captured using quantitative light-induced fluorescence, and a tooth image captured using transillumination,
wherein the first light source, the second light source, and the third light source are alternately arranged to surround the tooth image incident surface of the prism lens, and
wherein each of the first light source, the second light source, and the third light source comprises at least four light elements respectively disposed on four sides of the tooth image incident surface of the prism lens.

2. The device of claim 1, further comprising:
a long-distance image capturing unit coupled to the head part in an attachable and a detachable manner and provided with a reinforcing lens for long-distance image capturing at a portion covering the tooth image incident surface of the prism lens.

3. The device of claim 1, wherein the main body part is provided with a rechargeable battery rechargeable through a charging cradle.

* * * * *